United States Patent [19]

Wu

[11] Patent Number: 5,811,254

[45] Date of Patent: Sep. 22, 1998

[54] BROAD RANGE TOTAL AVAILABLE CHLORINE TEST STRIP

[75] Inventor: Wen H. Wu, Elkhart, Ind.

[73] Assignee: Integrated Biomedical Technology, Inc., Elkhart, Ind.

[21] Appl. No.: 822,570

[22] Filed: Mar. 19, 1997

[51] Int. Cl.$^6$ .............. C12Q 1/28; C12Q 1/26; C12Q 1/00; G01N 33/00
[52] U.S. Cl. ................. 435/28; 435/25; 435/4; 436/63; 436/101; 423/462; 423/500
[58] Field of Search ................. 435/28, 4, 25; 436/63, 101; 423/462, 500

[56] References Cited

U.S. PATENT DOCUMENTS

| | | | |
|---|---|---|---|
| 3,718,605 | 2/1973 | Storm | 252/408 |
| 4,049,382 | 9/1977 | Ross, Jr. et al. | 23/230 R |
| 4,071,317 | 1/1978 | Lam | 23/253 TP |
| 4,071,318 | 1/1978 | Lam | 23/253 TP |
| 4,071,321 | 1/1978 | Lam | 23/253 TP |
| 4,092,115 | 5/1978 | Rupe et al. | 23/230 R |
| 4,290,773 | 9/1981 | Magers et al. | 23/230 B |
| 4,318,984 | 3/1982 | Magers et al. | 435/14 |
| 4,339,242 | 7/1982 | Magers et al. | 23/230 B |
| 4,339,243 | 7/1982 | Magers et al. | 23/230 B |
| 4,340,392 | 7/1982 | Magers et al. | 23/230 B |
| 4,340,393 | 7/1982 | Magers et al. | 23/230 B |
| 4,340,394 | 7/1982 | Magers et al. | 23/230 B |
| 4,340,395 | 7/1982 | Magers et al. | 23/230 B |
| 4,380,585 | 4/1983 | Magers et al. | 436/66 |
| 4,904,605 | 2/1990 | O'Brien et al. | 436/169 |
| 4,938,926 | 7/1990 | Reiss | 422/58 |
| 5,300,442 | 4/1994 | Frant | 436/125 |
| 5,362,650 | 11/1994 | Harp | 436/125 |
| 5,491,094 | 2/1996 | Ramana et al. | 436/125 |

OTHER PUBLICATIONS

Johnson et al., "Stabilized neutral orthotolidine, SNORT, colormetric method for chlorine," *Analytical Chemistry*, 41, No. 13, 1744–1750 (1969). Month not Available.

Bauer et al., "Use of syringaldazine in a photometric method for estimating 'free' chlorine in water," *Analytical Chemistry*, 43, No. 3, 421–425 (1971). Month not Available.

Holland et al., "A safer substitute for benzidine in the detection of blood," *Tetrahedron*, 30, 3299–3301 (1974). Month not Available.

Standefer et al., "Use of tetramethylbenzidine in plasma hemoglobin assay," *Clin. Chem.*, 24, 4, 749–751 (1977). Month not Available.

Liem et al., "Quantatative determination of hemoglobin and cytochemical staining for peroxidase using 3,3',5,5'–tetramethylbenzidine dihydrochloride, a safe substitute for benzidine," *Analytical Biochemistry*, 98, 388–389 (1979). Month not Available.

Libermann, Jr. et al., "Development of the FACTS procedure for combined forms of chlorine and ozone in aqueous solutions," *American Chemical Society*, 14, No. 11, 1395–1400 (1980). Month not Available.

*Primary Examiner*—Louise N. Leary
*Attorney, Agent, or Firm*—Marshall, O'Toole, Gerstein, Murray & Borun

[57] ABSTRACT

A composition, method, and test device for determining the total available chlorine concentration of a test sample are disclosed. The test device includes a test pad having a suitable carrier matrix incorporating an indicator reagent composition capable of converting combined available chlorine to free available chlorine and of interacting with free available chlorine to produce a detectable and measurable response for total available chlorine over a range of 0 to over 5000 ppm total available chlorine in the test sample. An indicator reagent composition contains: (a) an indicator dye that is responsive to free available chlorine, such as tetramethylbenzidine, (b) a buffer, (c) a surfactant, (d) an optional catalyst, and (e) an optional polymer. An indicator reagent composition is incorporated into a carrier matrix, like filter paper, to provide a test pad useful in a dry phase total available chlorine assay of a test sample, such as a sanitizing solution for a hemodialysis unit.

32 Claims, No Drawings

BROAD RANGE TOTAL AVAILABLE CHLORINE TEST STRIP

FIELD OF THE INVENTION

The present invention relates to a composition, method, and test device for determining the total available chlorine concentration of a test sample. More particularly, the present invention relates to a method and test device for assaying a liquid test sample, such as a sanitizing solution, for total available chlorine concentration over the range of 0 to greater than 5000 ppm total available chlorine by using an improved indicator reagent composition. The indicator reagent composition undergoes a detectable and measurable response upon contact with a test sample containing free available chlorine. Contrary to prior compositions, the present indicator reagent compositions have the advantage of measuring a wide range of total available chlorine.

BACKGROUND OF THE INVENTION

The use of chlorine as a sanitizer or disinfectant for various water supplies and various types of equipment, like food processing equipment and medical equipment, such as a hemodialysis unit, is common. Because the amount of available chlorine in an aqueous solution relates directly to the disinfecting or sanitizing activity thereof, a test which rapidly and accurately measures available chlorine is important.

The available chlorine family is comprised of compounds which, when in aqueous solution, yield solutions of hypochlorous acid. The available chlorine family is further divided into compounds containing free available chlorine and compounds containing combined available chlorine. The sum of free available chlorine and combined available chlorine is termed total available chlorine.

Free available chlorine encompasses chlorine-containing compounds in aqueous solution such as hypochlorous acid, hypochlorite ion, and, in strong acid solutions, free chlorine. The use of free available chlorine as a disinfectant for water supplies and equipment is widespread because of its low cost, convenience, and effectiveness as an antiseptic agent in relatively low concentrations. For example, free available chlorine is used as a disinfectant in a majority of hemodialysis centers.

Combined available chlorine, also termed bound available chlorine, mainly encompasses organic chloramines, which release only a small amount of free available chlorine in aqueous solution. Conventionally, combined available chlorine has not been considered an effective disinfectant or sanitizer.

Accordingly, prior chlorine assays have focused on assays for free available chlorine, i.e., the active disinfectant. For example, assays disclosed in Rupe et al. U.S. Pat. No. 4,092, 115 and Ramana et al. U.S. Pat. No. 5,491, 094, consider combined available chlorine as an interferant in the assay for free available chlorine, and the assays have been designed only to measure free available chlorine. However, in some applications, it is important to assay for total available chlorine.

For example, chlorine is used in hemodialysis centers to sanitize hemodialysis units because chlorine is an effective and economical sanitizing agent. It is important to clean and disinfect a hemodialysis unit between each dialysis session to prevent pathogen contamination from patient to patient. However, chlorine also is a very toxic compound that can cause hemolysis even when only a trace amount of chlorine diffuses from the hemodialysis unit into the blood of an individual. Therefore, if an assay for residual chlorine in a hemodialysis unit detects only free available chlorine, a potentially toxic amount of combined available chlorine, which slowly generates free available chlorine, can be present to adversely affect an individual subsequently connected to the hemodialysis unit. Trace amounts of free available chlorine also can adversely affect filtration membranes of the hemodialysis unit.

Therefore, when a sanitizing solution is used in medical or food processing equipment, two critical chlorine levels must be monitored. First, the free available chlorine concentration must be sufficiently high to perform a sanitizing or disinfecting function, i.e., at least about 1000 ppm (parts per million) free available chlorine is needed to effectively sanitize equipment. Typically, a chlorine concentration sufficient for equipment sanitization is about a 1 to 10 volume dilution of a 5.25% (by weight) sodium hypochlorite with water, to provide a solution containing about 0.5% to about 0.6% (by weight) sodium hypochlorite, i.e., about 5000 to about 6000 ppm chlorine. During the sanitizing process, the sanitizing solution is assayed periodically to ensure that sufficient free available chlorine is present to sanitize the equipment.

After the sanitizing function is completed, and before use, the equipment is rinsed with water to flush residual chlorine from the equipment. The rinse water also is assayed for available chlorine to ensure that the level of residual available chlorine is below the maximum allowable level, e.g., 0.5 ppm as recommended by the Association of Advancement of Medical Instrumentation (AAMI). In practice, the residual available chlorine concentration is essentially zero, or at least below the lowest detectable levels of about 0.1 to about 0.2 ppm, i.e., equivalent to a 1 to 100,000 water dilution of 5.25(by weight) sodium hypochlorite.

Presently, only two types of commercial assay systems are suitable for assaying hemodialysis units for available chlorine. One assay utilizes tablets or dry powder, and the other utilizes dry chemistry dip strips. Each assay has advantages and disadvantages, and neither assay satisfies the different testing requirements needed for a hemodialysis unit.

The tablet method has good sensitivity (e.g., 0.1 ppm) and is less expensive per assay. However, the tablet method is more cumbersome to perform and requires more technician time. The dry chemistry test strips are usually not as sensitive as the tablet method and can cost more per test. Nevertheless, the strip test is very easy and convenient, particularly when operating a mobile hemodialysis unit. In most hemodialysis centers, the test strip is used as a screening test for residual chlorine, whereas the tablet method is used for more critical water testing. Because of the differences in test requirements, most hemodialysis centers are forced to stock both the tablet and dry chemistry test systems.

To date, no known single assay is available to assay both the high and the low available chlorine concentration range because the 10,000 fold difference in chlorine concentration between a working sanitizing solution and a residual chlorine concentration makes detection and differentiation of concentration levels difficult. The present invention is directed to providing a single assay for total available chlorine that is capable of measuring total available chlorine concentration over the range of 0 to greater than 5000 ppm, and especially 0 to greater than 1000 ppm.

The present invention, therefore, is directed to an assay method and device that can be used to test: (a) a working sanitizing solution, containing 500 ppm or more of free available chlorine, without diluting the solution, and (b) residual chlorine, both free and bound available chlorine, present at 0.5 ppm or less in rinse water. Accordingly, a test strip can be used either to test for residual chlorine in the rinse water after cleaning the hemodialysis unit, or to test for the available chlorine content of a working solution. As illustrated hereafter, the present test strips have a good sensitivity and a wide detection range with a continuous color response from 0.5 to over 1000 ppm total available chlorine.

The present method of assaying for total available chlorine in an aqueous test sample yields trustworthy and reproducible results by utilizing an indicator reagent composition that undergoes a color transition in response to total available chlorine concentration, and not as a result of a competing chemical or physical interaction, such as a preferential interaction with another test sample component. For example, the present indicator reagent composition has sufficient sensitivity to detect as little as 0.1 ppm total available chlorine. Additionally, the method and composition utilized in the total available chlorine assay does not adversely affect or interfere with any other test reagent pads that are present on a multiple test pad strip.

In accordance with the present invention, an indicator reagent composition can be incorporated into a carrier matrix to provide sufficient sensitivity and color differentiation to assay for total available chlorine concentration over the range of 0 ppm to greater than 5000 ppm, and typically greater than 1000 ppm. In addition, although dry phase test strips have been used to assay for chlorine concentration, no dry phase test strip has been used to assay for total available chlorine over such a wide concentration range. Examples of prior disclosures relating to assaying for chlorine include Storm U.S. Pat. No. 3,718,605; Reiss U.S. Pat. No. 4,938,926; Ross, Jr. et al. U.S. Pat. No. 4,049,382; Frant U.S. Pat. No. 5,300,442, Harp U.S. Pat. No. 5,362,650; O'Brien et al. U.S. Pat. No. 4,904,605; and J. D. Johnson et al., *Analytical Chemistry*, 40(13), pages 1744–1750 (1969).

SUMMARY OF THE INVENTION

In brief, the present invention is directed to a new and improved composition, test device, and method of determining the total available chlorine concentration of a test sample. A device includes a test pad comprising a suitable carrier matrix incorporating an indicator reagent composition capable of converting combined available chlorine to free available chlorine, and interacting with free available chlorine to produce a detectable response to total available chlorine concentration. A carrier matrix of the test pad comprises a bibulous material, such as filter paper; a nonbibulous material, such as a strip, layer, or membrane of a polymerized material; or a mixture thereof. An indicator reagent composition is homogeneously incorporated into the carrier matrix, and the carrier matrix then holds the indicator reagent composition homogeneously throughout the carrier matrix while maintaining carrier matrix penetrability by the test sample.

More particularly, the present invention is directed to a method of assaying for the total available chlorine content of aqueous test samples by utilizing a new indicator reagent composition. It has been demonstrated that a reagent composition including: (a) an indicator capable of interacting with free available chlorine to provide a detectable and measurable response, (b) a buffer, like a polycarboxylic acid, (c) a surfactant, like an anionic surfactant, (d) an optional catalyst, and (e) an optional polymer, affords sufficient sensitivity to test sample total available chlorine content, and a sufficient color differentiation between test samples of different total available chlorine content over the range of 0 to greater than 5000 ppm, and particularly 0 to greater than 1000 ppm. In accordance with an important feature of the present invention, the indicator reagent composition has a pH of about 5 to about 6, and in preferred embodiments contains a catalytic amount of iodide ion or a peroxidase enzyme.

In accordance with an important feature of the present invention, an accurate and reliable quantitative determination for total available chlorine in a test sample is achieved because the indicator reagent composition is maintained at a pH of about 5 to about 6, and optionally contains an iodide ion or peroxidase catalyst. By utilizing an indicator reagent composition of the present invention, the quantitative assay for total available chlorine in liquid test samples is more sensitive and accurate because the combined available chlorine in the test sample is quickly converted to free available chlorine. The indicator reagent composition then is able to detect the total available chlorine present in the test sample.

Therefore, a buffer is included in the indicator reagent composition to maintain a pH of about 5 to about 6 and achieve a more accurate measurement of the total available chlorine concentration of the test sample. The buffer is included in the indicator reagent composition to maintain the reagent composition within a pH range wherein the combined available chlorine, i.e., chloramine, is quickly converted to free available chlorine. The presence of a catalytic amount of iodide ion or a peroxidase enzyme further facilitates, and speeds, conversion of combined available chlorine to free available chlorine.

Therefore, one aspect of the present invention is to provide a method and composition for quantitatively determining the total available chlorine concentration of an aqueous liquid. The composition converts the combined available chlorine to free available chlorine, and interacts with the free available chlorine to produce a change in color of a test device that is indicative of the total available chlorine concentration of the test sample.

Another aspect of the present invention is to provide a method of assaying aqueous test samples, said method having sufficient sensitivity and sufficient visual color resolution to allow differentiation between, and the quantitative measurement of, test samples having different total available chlorine concentrations.

Yet another object of the present invention is to provide a sensitive method of assaying test samples for total available chlorine concentration over the range of 0 to greater than 5000 ppm total available chlorine. Accordingly, the present method is able to detect residual chlorine present in rinse water, i.e., less than 0.5 ppm, or working concentration of free available chlorine above 1000 ppm.

Another aspect of the present invention is to provide an indicator reagent composition that interacts with free available chlorine and undergoes a visually or instrumentally differentiable color transition to allow the determination of total available chlorine concentration of a test sample.

Another aspect of the present invention is to provide a method of assaying for the total available chlorine content of a liquid test sample by incorporating an indicator reagent composition into a dry phase detection device, wherein the indicator reagent composition comprises: (a) an indicator capable of interacting with free available chlorine to provide a detectable and measurable response, (b) a buffer, (c) a surfactant, (d) an optional catalyst, (e) an optional polymer, and (f) a suitable carrier, and wherein the indicator reagent composition has a pH of about 5 to about 6.

Still another aspect of the present invention is to provide a new and improved method of assaying for the total available chlorine content of an aqueous test sample by utilizing a test device, including a carrier matrix, said carrier matrix comprising a bibulous matrix, like filter paper, or a nonbibulous matrix, like a glass fiber or a layer of a permeable polymeric material, and said carrier matrix having incorporated therein an indicator reagent composition capable of converting bound available chlorine to free available chlorine, and of interacting with free available chlorine present in the test sample, to provide a color transition that can be correlated to the total available chlorine concentration of the test sample.

A further aspect of the present invention is to provide an improved dry phase test strip that incorporates an indicator reagent composition comprising a suitable indicator, a buffer, and a surfactant, and having a pH of about 5 to about 6, into the carrier matrix, and thereby provide a quantitative assay for the total available chlorine content of a test sample.

The above and other aspects and advantages and novel features of the present invention will become apparent from the following detailed description of the preferred embodiments.

DETAILED DESCRIPTION OF THE PREFERRED EMBODIMENTS

In accordance with the method of the present invention, a quantitative assay of aqueous test samples for total available chlorine is accomplished by utilizing an indicator reagent composition that includes (a) an indicator capable of interacting with free available chlorine to provide a detectable and measurable response, (b) a buffer, (c) a surfactant, (d) an optional catalyst, and (e) an optional polymer. By employing an indicator reagent composition of the present invention, having a pH of about 5 to about 6, sufficient sensitivity and sufficient visual color differentiation between test samples of different total available chlorine content is achieved. In accordance with the method of the present invention, test samples having a total available chlorine content of 0 to greater than 5000 ppm, and particularly 0 to greater than 1000 ppm, can be measured and differentiated.

To achieve the full advantage of the present invention, the method and composition are employed in dry phase, test pad assays to determine the total available chlorine concentration of aqueous test samples. A dry phase test strip, including a test pad comprising a carrier matrix incorporating an indicator reagent composition of the present invention, allows the rapid quantitative assay of test samples by visual means.

In particular, the present invention allows determination of the total available chlorine concentration of a test sample by the visual color change of a test pad on a test strip resulting from contact between the test strip and the test sample. Total available chlorine concentration of the test sample is determined by correlating the detected free available chlorine concentration to the total available chlorine concentration of the test sample. The test strip includes a test pad comprising an inert carrier matrix incorporating an indicator reagent composition. The present composition and method allow the rapid colorimetric determination of the total available chlorine concentration of a test sample by quickly converting the bound available chlorine to free available chlorine, and assaying for the resulting total free chlorine concentration. Previous assay methods employed compositions that avoided measurement of bound available chlorine. In contrast, the present method measures the total available chlorine content, i.e., free and bound available chlorine, by utilizing a composition having a pH of about 5 to about 6, and which optionally contains a catalyst to increase the rate of conversion of combined available chlorine to free available chlorine.

An important component of the present indicator reagent composition is the indicator. The indicator included in the indicator reagent composition is limited only in that the indicator is capable of undergoing a detectable response, and preferably a chromogenic response, in the presence of free available chlorine. Accordingly, the indicator preferably is a redox indicator that undergoes a color transition, or other detectable response, upon conversion from its reduced state to its oxidized state by free available chlorine. The indicator dye should be sufficiently stable such that free available chlorine is present before a color transition occurs. To achieve the full advantage of the present invention, the indicator dye undergoes a color transition through various detectable and measurable degrees and intensities of color such that the degree and intensity of the color transition can be correlated to the concentration of total available chlorine in a test sample.

It should be noted that the indicator is incapable of interacting with bound available chlorine. Therefore, as explained in detail hereafter, the bound available chlorine is converted to free available chlorine. The indicator, therefore, responds to the total available chlorine concentration of the test sample.

The indicator, therefore, typically is a redox indicator. Preferred redox indicators are the benzidine-type indicators, i.e., benzidine and benzidine derivatives. The benzidine-type indicators have the ability to develop easily detectable and differentiable color hues of varying intensity, which makes these indicators useful in quantitative assays. Although the exact mechanism of color formation by benzidine-type indicators in the presence of various analytes is not known, it is known that two sequentially color forms occur: a first colored species which is blue in color, and a second colored species, which is brown. The blue color species tends to be transient and changes to the brown color species. Therefore, it has been necessary to detect a color change within a prescribed time period or to stabilize the blue color. Otherwise, the significance of the color transition, i.e., correlation to analyte concentration, is lost because subtle shades of blue, which are easily distinguishable, yield to the less easily differentiated brown hues.

Benzidine-type indicators have the structure:

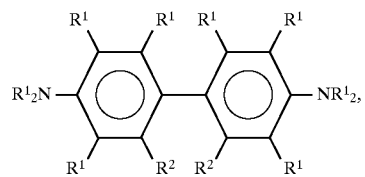

wherein the $R^1$ and $R^2$ substituents, same or different, can be hydrogen, lower alkyl (i.e., alkyl having 1 to about 6 carbon atoms), lower alkyloxy (i.e., alkyloxy having 1 to about 6 carbon atoms), amino, aryl, or aryloxy. Moreover, the $R^2$ substituents together can form $-(CH_2)_n-$, wherein n is 1 or 2. In addition to the above, the $R^1$ and $R^2$ groups can be substituted such as with hydroxy, halogen, cyano, and similar substituents. Typical benzidine-type indicators include, but are not limited to, benzidine, o-tolidine, o-dianisidine, 2,7-diaminofluorene, 3,3',5,5'-tetramethylbenzidine (hereafter tetramethylbenzidine or TMB), 3,3'-diaminobenzidine, 3,3',5,5'-tetra(alkyl)benzidine, the various N- and N'-substituted benzidines and others, and mixtures thereof.

Another useful class of dyes are the heterocyclic azine indicators, for example, bis(N-ethylquinol-2-one)azine and (N-methylbenzthiozal-2-one)(1-ethyl-3-phenyl-5-methyltriazol-2-one)azine. Preferably, the indicator is a benzidine-type indicator. To achieve the full advantage of the present invention, the indicator is 3,3',5,5'-tetramethylbenzidine.

The indicator typically is present in the indicator reagent composition in a concentration of about 1 to about 200 mM, and preferably in a concentration of about 10 to about 150 mM. The amount of indicator in the indicator reagent composition can be less than about 1 mM, or greater than about 200 mM, depending upon the intensity of the color transition that a particular indicator undergoes upon oxidation. In general, the amount of indicator included in the indicator reagent composition is limited only in that the indicator undergoes a detectable color transition in proportion to the concentration of free available chlorine. The detection of free available chlorine then can be correlated to total available chlorine content of the test sample.

In addition to the indicator, the indicator reagent composition also contains a buffer. In accordance with an important feature of the present invention, the buffer buffers the indicator reagent composition in the range of about 5 to about 6, and preferably about 5 to about 5.5. In the pH range of about 5 to about 6, the bound available chlorine, i.e., chloramine, is converted to free available chlorine at a sufficient rate such that the bound available chlorine is assayed and detected by the present indicator reagent composition.

A pH of about 5 to about 6, therefore, provides an indicator reagent composition having a very high sensitivity to chlorine. Free available chlorine interacts with an indicator over the pH range of about 6 to about 9. However, bound available chlorine cannot interact with the indicator above pH about 6. The interaction between bound available chlorine and the indicator increases significantly at pH about 5.5, i.e., bound available chlorine is converted to free available chlorine, which in turn can interact with the indicator. However, below pH about 5, the development of a background color increases significantly. This background color interferes with an accurate assay for total available chlorine. Therefore, to achieve the full advantage of the present invention, the indicator reagent composition is buffered at a pH of about 5.1 to about 5.5.

The identity of the buffer is not particularly limited, as long as the indicator reagent composition is buffered in the range of about 5 to about 6. Therefore, useful buffers include, but are not limited to, polycarboxylic acids, phosphate, borate, acetate, and mixtures thereof. Preferred buffers are polycarboxylic acids, and especially polycarboxylic acids wherein the carboxyl groups are separated by two to five carbon atoms. Examples of useful polycarboxylic acid buffers include, but are not limited to, citric acid, succinic acid, lactic acid, and ketoglutaric acid. As demonstrated in detail hereafter, the polycarboxylic acid buffers improve the color response of the indicator to free available chlorine, and provide a more stable color response. It has been theorized, but is not relied upon herein, that the polycarboxylic acid is capable of complexing with the indicator to form a brighter and more spectacular color, and to stabilize the color. The concentration of buffer in the composition typically is about 20 to about 600 mM, and preferably about 50 to about 200 mM.

In addition to the indicator and the buffer, the indicator reagent composition also contains a surfactant, in particular an anionic surfactant or a nonionic surfactant. The surfactant is present in the indicator reagent composition in an amount of about 0.05% to about 1.5%, and preferably about 0.1% to about 1%, by weight of the composition. To achieve the full advantage of the present invention, the surfactant is present in an amount of about 0.15% to about 0.5% by weight of the composition.

As illustrated in detail hereafter, the surfactant not only improves the ability of the test sample to wet the carrier matrix, but the surfactant also improves the stability of the color transition of the indicator in response to free available chlorine. As further illustrated hereafter, the surfactant helps permit the present indicator reagent composition to assay for a broad range of total available chlorine, i.e., 0 ppm to greater than 5000 ppm.

With respect to wetting and color stabilization for test samples containing 0 to about 20 ppm total available chlorine, the surfactant can be an anionic, or a nonionic, surfactant. Each of these classes of surfactants effectively stabilizes the light blue to blue color provided by the indicator. Cationic surfactants and zwitterionic surfactants, as demonstrated hereafter, did not stabilize the color transition.

With respect to color stabilization for test samples containing greater than about 20 ppm total available chlorine, the surfactant typically comprises an anionic surfactant. Anionic surfactants allowed the indicator reagent composition to successfully assay test samples having a total available chlorine concentration of 20 ppm or greater, up to about 5000 ppm. However, a nonionic surfactant is preferred if the buffer is lacking a polycarboxylic acid.

Useful nonionic surfactants include, but are not limited to, an ethoxylated polysorbate, e.g., polysorbate 20 through polysorbate 85, an ethoxylated alcohol, e.g., a $C_{10}$ to $C_{22}$ alcohol ethoxylated with about 10 to about 25 moles of ethylene oxide, an ethoxylated phenol, i.e., an ethoxylated octylphenol, nonylphenol, or dodecylphenol with about 8 to about 30 moles of ethylene oxide, a polyethylene glycol, e.g., PEG-8 through PEG-40, a polypropylene glycol, e.g., PPG-9 through PPG-34, an ethylene glycol-propylene glycol copolymer, e.g., a poloxamer, a polybutylene glycol, and similar nonionic surfactants, and mixtures thereof. In general, a useful nonionic surfactant has an HLB value of about 6 to about 25.

Anionic surfactants useful in the present invention are not particularly limited. Usually, the anionic surfactant includes a hydrophobic moiety, such as a carbon chain including about eight carbon atoms to about 30 carbon atoms, and particularly about twelve carbon atoms to about twenty carbon atoms; and further includes a hydrophilic moiety, such as sulfate, sulfonate, carbonate, phosphate, or carboxylate. Often, the hydrophobic carbon chain is etherified, such as with ethylene oxide or propylene oxide, to impart a particular physical property or reduced surface tension, to the anionic surfactant.

The anionic surfactants are well known, and can be a fatty acid, a salt of a fatty acid, an ethoxylated fatty acid, or a salt of an ethoxylated fatty acid, for example. Therefore, suitable anionic surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta-alkyloxy alkane sulfonates, alkyl arylsulfonates, alkyl carbonates, alkyl ether carboxylates, fatty acids, sulfosuccinates, alkyl ether sulfosuccinates, sarcosinates, octoxynol phosphates, nonoxynol phosphates, taurates, fatty taurides, sulfated monoglycerides, fatty acid amido polyoxyethylene sulfates, and isothienates; or mixtures thereof. Many additional anionic surfactants are described in *McCutcheon's, Detergents and Emulsifiers,* 1993 *Annual,* published by McCutcheon Division, MC Publishing Co., and incorporated herein by reference.

Usually, the anionic surfactant is present in the composition as a neutralized salt in the form of a sodium, potassium, lithium, ammonium, alkylammonium, or hydroxyalkylammonium salt, wherein the alkyl moiety includes one to about three carbon atoms. The alkyl sulfates and alkyl ether sulfates are particularly effective classes of anionic surfactants. Consequently, exemplary anionic surfactants useful in the composition and method of the present invention include, but are not limited to, the ammonium, monoethanolamine, diethanolamine, triethanolamine, isopropylamine, sodium, potassium, lithium, or magnesium salt of lauryl sulfate, dodecylbenzenesulfonate, lauryl sulfosuccinate, lauryl ether sulfate, lauryl ether carboxylate, lauryl sarcosinate, cocomethyl tauride, and sulfosuccinate half ester amide; or mixtures thereof. Examples of especially useful anionic surfactants are a lauryl sulfate salt, a lauryl ether sulfate salt, a lauryl phosphate, a sulfosuccinate salt, a dodecylsulfonate salt, a cholate salt, a $C_8$ to $C_{18}$ fatty acid, and mixtures thereof.

In addition to the indicator, buffer, and surfactant, the indicator reagent composition also optionally can contain 0 to about 1000 ppm of a catalyst to increase the rate at which the indicator reagent composition converts the combined available chlorine to free available chlorine, thereby making it possible to assay for the amount of combined and free, i.e., total, available chlorine in the test sample.

In one embodiment, the catalyst is a peroxidase, like horseradish peroxidase. The peroxidase catalyst is present in the indicator reagent composition in an amount of 0 to about 1000 ppm. The peroxidase reduces the interference of ammonium ions in the total available chlorine assay. It is important to reduce ammonium ion interference because ammonium ions react with free available chlorine to form a chloramine, and thereby convert free available chlorine to bound available chlorine. The presence of a peroxidase reverses this reaction, and frees the bound available chlorine from chloramine such that the resulting free available chlorine is available for assay by a present indicator reagent composition.

The finding that a peroxidase stabilizes and enhances color formation in a total available chlorine assay is both new and unexpected. It was expected that a peroxidase, which is a protein, would interfere in the reaction between free available chlorine and the indicator. This interference is expected because free available chlorine reacts with nitrogen present in a protein to form a chloramine, which binds chlorine and makes it unavailable for reaction with the indicator. Surprisingly, however, it was found that incorporating a catalytic amount of a peroxidase into a present indicator reagent composition does not interfere with the reaction between the indicator and free available chlorine and thereby reduce test strip sensitivity, but, to the contrary, increases the sensitivity of the test strips and yields an accurate quantitative assay for total available chlorine.

In particular, the effect of incorporating horseradish peroxidase is illustrated below. Free available chlorine reacts with variety of redox indicators, the most common of which are benzidine indicators, such as orthotolidine or 3,3',5,5'-tetramethylbenzidine. An important problem associated with such indicators is that they exhibit a very narrow sensitivity range for chlorine, i.e., there is no variation of test strip color when chlorine level is 10 ppm or higher. Therefore, it is impossible to visually quantify a chlorine level greater than about 10 ppm. However, by adding horseradish peroxidase to an indicator reagent composition, the test strip color varies over the range 0 ppm to greater than 1000 ppm total available chlorine with a differentiable color transition from colorless to light blue to dark blue to greenish brown to brown. Distinct color separation differentiation was observed for free available chlorine levels of 0, 0.5, 1, 5, 10, 100, 300, 500, and 1000 ppm.

In particular, two indicator reagent compositions were prepared and incorporated into individual test strips. The indicator reagent compositions were identical, except one composition contained horseradish peroxidase. When the peroxidase was absent, the test strips turned brown when the free available chlorine content was 10 ppm or greater. When the peroxidase was present, the test strips changed color from very light blue to light blue, blue, darker blue, dark blue, black blue, greenish brown, and brown in response to free available chlorine levels of 0.5, 1, 5, 10, 100, 300, 500, 1000 ppm, respectively.

In another test, it was found that peroxidase increases the rate of conversion of combined available chlorine to free available chlorine. It was found that a test strip incorporating an indicator reagent composition lacking peroxidase reacted very slowly with a test sample containing 1 ppm of chloramine. However, when peroxidase was incorporated into the composition, a test strip reacted with 1 ppm of chloramine in 45 seconds to generate a color transition identical to 1 ppm of free available chlorine.

Incorporating a peroxidase into an indicator reagent composition provides another advantage. In particular, when peroxidase is present, the test strip can be used to assay for peroxide in addition to total available chlorine. Hydrogen peroxide is a commonly used disinfectant for hemodialysis units, but most indicator reagent compositions are insensitive to peroxide unless a catalytic peroxidase enzyme is present.

Accordingly, a present test strip can be used to assay for peroxide over the range of about 0.1 to about 400 ppm. This capability greatly increases versatility of the present test strips because medical workers often use hydrogen peroxide to sanitize hemodialysis units. The present test strips, therefore, can be used by medical personnel as the sole test strip to assay for residual sanitizing compounds in the rinse water of a hemodialysis unit, regardless of whether the sanitizer is chlorine or a peroxide. Medical laboratories and clinics, therefore, do not have to stock different types of assay kits for testing low total available chlorine, high total available chlorine, and peroxide. Similar to testing for low, residual amounts of chlorine, the present test strips turn blue upon contact with a test sample containing residual peroxide. A single test strip, therefore, provides the convenience of a dual test system for hydrogen peroxide and total available chlorine.

In another embodiment, the catalyst is iodide ion, typically in the form of an alkali metal iodide, like lithium iodide, sodium iodide, or, preferably, potassium iodide. An excess amount of iodide ion can interfere with the assay. Therefore, when iodide ion is used as the catalyst, the amount of iodide ion present in the indicator reagent composition is 0 to about 20 ppm, and preferably 0 to about 10 ppm. To achieve the full advantage of the present invention, the amount of iodide ion present in the composition is 0 to about 5 ppm. It has been determined that as little as 1 ppm of iodide ion can react with at least four equivalents of chloramine, thereby increasing the rate of conversion of bound available chlorine to a detectable free chlorine species.

Iodide ion allows an indirect assay of the bound available chlorine. In particular, the catalytic mechanism involves recycling of iodide ion and iodine. The iodide ion first is oxidized by chloramine to iodine, which in turn oxidizes an indicator, like tetramethylbenzidine (TMB), to an oxidized, colored indicator complex. As a result, iodine is reduced back to iodide ion which then repeats the oxidation-reduction cycle until all of the chloramine substrate is consumed. Like any catalytic reaction, the rate of this conversion is proportional to the level of catalyst. At a potassium iodide concentration of 0.5 ppm, a reaction to completely convert 5 ppm of chloramine takes about 50 seconds. At a potassium iodide concentration of 2 ppm, however, completion of the reaction is almost instantaneous.

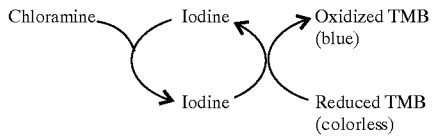

In accordance with an important feature of the present invention, the amount of iodide ion, therefore, can be maintained at a very low level to perform its intended function, and, at the same time, not interfere with the assay for total available chlorine. If the amount of iodide ion is too high, iodine can be formed too rapidly and precipitated before the iodine can react with the indicator. As a consequence, the intensity of color transition is reduced, and a low assay results. At the same time, the yellow/brown color of iodine causes strip color to shift to a dirty green hue, making color differentiation to correlate the color transition to total available chlorine concentration more difficult.

An optional polymer also can be incorporated into the indicator reagent composition. The polymer improves the stability and uniformity of the color transition of the test device. The polymer also helps incorporate the indicator reagent composition uniformly throughout the carrier matrix. Suitable polymers include, but are not limited to, polyvinylpyrrolidone, polyvinyl alcohol, gum arabic, gelatin, algin, carrageenan, casein, albumin, methyl cellulose, and similar natural and synthetic polymeric materials. Specific examples of natural, cellulose-type polymers are hydroxypropylcellulose, hydroxyethylcellulose, hydroxybutylcellulose, and sodium carboxymethylcellulose. A useful synthetic polymer is a polyvinylpyrrolidone pyrrolidone of average molecular weight about 40,000 and available commercially from ISP Corp., Wayne, N.J. A polymer generally is included in the indicator reagent composition in an amount ranging from 0% to about 4%, and preferably from about 0.2% to about 3%, by total weight of the indicator reagent composition.

The natural, cellulose-type polymers are preferred over synthetic polymers, like polyvinylpyrrolidone, because the synthetic polymers have a tendency to impart a green hue to the test strip. The cellulose-type polymers impart a preferred bluish color. The polymers also serve a thickening function to help facilitate impregnation of the carrier matrix with the indicator reagent composition.

The presence of a polymer in an indicator reagent composition also enhances chloramine reactivity. The effectiveness of a polymer with respect to enhancing chloramine reactivity is directly related to the hydrophobicity of the polymer. For example, GANTREZ ES225 (an ethyl ester of a PVM/MA copolymer), KLUCEL (hydroxypropylcellulose), and PVP K60 (polyvinylpyrrolidone) have a decreasing effectiveness with respect to enhancing chloramine reactivity, and also have a decreasing hydrophobicity. Test strips impregnated with an indicator reagent composition containing GANTREZ ES225 were essentially 100% reactive with chloramine, but also tended to develop background color with chlorine-free water. PVP K60 generated little background color, but is only 50% reactive with chloramine. KLUCEL provided the best overall results when considering both chloramine reactivity and lack of background color. In particular, when using KLUCEL, the test strip had an 80% to 90% chloramine reactivity and no background color.

The above-mentioned chloramine reactivities were evaluated by comparing the color of a test strip after immersion into hypochlorite (free chlorine) solutions either containing or free of ammonium sulfate. The addition of ammonium ions to the hypochlorite solution converts hypochlorite to chloramine, which consequently is unreactive to free chlorine test strips. Test strip reactivity to chloramine can be improved and restored to 100% by various approaches described herein, including a pH of about 5 to 6, the presence of a surfactant, the presence of a catalyst, and/or the presence of a polymer. The percent reactivity was visually estimated by comparing the intensity of test strip color with chloramine in relationship to the equivalent test strip color with free chlorine.

In addition, if necessary or if desired, inert background dyes can be included in the reagent composition to improve the color resolution and differentiation of the color transition in the present assay for total available chlorine. Suitable background dyes include, but are not limited to, ethyl orange (4-(4-diethylaminophenylazo)benzenesulfonic acid); Orange G (4-(2-hydroxy-(7,9 sodium disulfonate)-1-naphthylazo)-benzene); disperse orange 11, 13, or 25; calcomine orange; methyl orange; and orange II (4-(2-hydroxy-1-naphthylazo)benzenesulfonic acid), or mixtures thereof. A background dye is included in an indicator reagent composition of the present invention in a concentration of 0 mM to about 2 mM, and preferably 0 mM to about 1 mM.

The carrier for the ingredients of an indicator reagent composition includes water. However, because of the limited water solubility of particular ingredients included in the indicator reagent composition, organic solvents, such as acetone, methanol, ethanol, isopropyl alcohol, ethylene glycol, propylene glycol, dimethylformamide, dimethylsulfoxide, acetonitrile, ethyl acetate, and similar solvents can be included in the carrier vehicle. The selection of a suitable organic solvent or solvents, in addition to water, to include in the carrier of the indicator reagent composition is within the capability of those skilled in the art of designing diagnostic assays.

The amount of organic solvent present in an indicator reagent composition generally is 0% to about 90%, and preferably about 10% to about 70%, by weight of the carrier. A carrier comprising water and an organic solvent, like methanol, ethanol, or acetone, is especially preferred because a carrier matrix impregnated with the indicator reagent composition can be dried within a few to several minutes.

As previously described, an indicator reagent composition undergoes a color transition upon contact with a test sample to provide an assay for total available chlorine concentration from the intensity and degree of the color transition. In accordance with an important feature of the present invention, an indicator reagent composition of the present invention provides a sufficiently resolved and differentiated color transition such that the total available chlorine in a test sample can be measured and accurately determined without the use of color-measuring instruments, such as spectrophotometers or calorimeters, over a concentration range of 0 to greater than 5000 ppm. However, if desired, such color-measuring instruments can be used to measure the difference in color degree and intensity between the test sample and a solution having a known concentration of total available chlorine.

The intensity and degree of the color transition are used to determine the total available chlorine content of the test sample by comparing or correlating the color produced by the test sample to colors produced by solutions having a known total available chlorine concentration. In accordance with an important feature of the present invention, the indicator reagent composition provides a sufficiently resolved and differentiated color transition such that the total available chlorine of the test sample can be measured for test samples having a total available chlorine content of 0 to greater than about 5000 ppm without the use of color-measuring instruments.

An indicator reagent composition of the present invention, as described above, is used in dry phase, test pad assays for total available chlorine. The dry phase, test pad assay for total available chlorine utilizing a present indicator reagent composition is performed in accordance with methods well known in the art. In general, the assay for total available chlorine is performed by contacting the test sample with an analyte detection device that includes an indicator reagent composition. The analyte detection device can be dipped into the test sample, or the test sample can be applied to the analyte detection device dropwise. The resulting change in color of the analyte detection device reveals the total available chlorine concentration of the test sample; and, if so designed, the resulting color transition can be compared to a standardized color chart to provide a measurement of the total available chlorine concentration of the test sample.

Typically, the analyte detection device is a test strip impregnated with an indicator reagent composition, designed either as a single pad test strip (to assay only for a single analyte) or as a multiple pad test strip (to assay for several analytes simultaneously). For either type of test strip, the test strip includes a support strip, or handle, normally constructed from a hydrophobic plastic, and a reagent test pad, comprising a bibulous or nonbibulous carrier matrix. In general, the carrier matrix is an absorbent material that allows the test sample to move in response to capillary forces through the matrix to contact the indicator reagent composition and produce a detectable and measurable color transition.

The carrier matrix can be any substance capable of incorporating the chemical reagents required to perform the assay of interest, as long as the carrier matrix is substantially inert with respect to the chemical reagents. The carrier matrix also is porous or absorbent relative to the liquid test sample.

The expression "carrier matrix" refers either to bibulous or nonbibulous matrices that are insoluble in the carrier of the indicator reagent composition and other physiological fluids and that maintain their structural integrity when exposed to the carrier and other physiological fluids. Suitable bibulous matrices include filter paper, sponge materials, cellulose, wood, woven and nonwoven fabrics, and the like. Nonbibulous matrices include glass fiber, polymeric films, and microporous membranes. Other suitable carrier matrices include hydrophilic inorganic powders, such as silica gel, alumina, diatomaceous earth and the like; argillaceous substances; cloth; hydrophilic natural polymeric materials, particularly cellulosic material, like cellulose beads, and especially fiber-containing papers such as filter paper or chromatographic paper; synthetic or modified naturally occurring polymers, such as cellulose acetate, polyvinyl chloride, polyacrylamide, polyacrylates, polyurethanes, crosslinked dextran, agarose, and other such crosslinked and noncrosslinked water-insoluble hydrophilic polymers. The carrier matrix can be of different chemical compositions or a mixture of chemical compositions. The matrix also can vary in regards to smoothness and roughness combined with hardness and softness. The handle usually is formed from hydrophobic materials such as cellulose acetate, polyethylene terephthalate, polycarbonate, or polystyrene, and the carrier matrix is most advantageously constructed from filter paper or polymeric films.

The carrier matrix of the test strip can be any bibulous or nonbibulous material that allows permeation by the test sample to saturate the test pad of the test strip that is impregnated with the indicator reagent composition. A preferred carrier matrix is a hydrophilic, bibulous matrix, including cellulosic materials, such as paper, and preferably filter paper. The carrier matrix also can be a hydrophilic, nonbibulous matrix, including polymeric films, such as a polyurethane or a crosslinked gelatin. Such polymeric films possess all of the qualities required of a carrier matrix of the present invention, including suspending and positioning both the essential ingredient and any optional ingredients included in the indicator reagent composition, and permeability of the test sample through the carrier matrix.

In accordance with the method of the present invention, to perform a dry phase test strip assay for total available chlorine, an acetone solution, including: (a) about 1 to about 200 mM of an indicator, such as tetramethylbenzidene; (b) about 0.05% to about 1.5% by weight of a surfactant, like a sulfosuccinate; (c) 0% to about 4% by weight of a polymer, like a cellulose-type polymer; and (d) any other desired optional ingredients, or solvents, first is prepared. A nonbibulous matrix, such as a polyurethane film, or a bibulous matrix, such as filter paper, then is saturated or impregnated with the acetone solution by immersing or by spraying the acetone solution onto sheets or precut strips or pads of the polyurethane film or filter paper.

Then, after removing the acetone solvent by drying in a forced air oven at a temperature of about 40° C. to about 100° C. for about 2 minutes to about 5 minutes, the polyurethane film or filter paper is saturated and impregnated with an aqueous solution, including: (a) about 20 to about 600 mM of a buffer, like a citrate buffer; (b) 0 to 1000 ppm of a catalyst, like a peroxidase or iodide ion; (c) 0% to about 4% by weight of a polymer; and (d) any other desired optional ingredients, surfactants, or solvents, like background dyes, either by immersion or by spraying. After a second oven drying at about 40° C. to about 100° C. for approximately 2 minutes to 15 minutes, the twice-saturated or twice-impregnated polyurethane film or filter paper, if necessary, is cut to an appropriate size, such as a pad having dimensions from about 0.2 in. (inch) (0.5 cm) by about 0.5 in (1.3 cm) to about 0.5 in. (1.3 cm) by about 1 in. (2.5 cm).

It should be understood that it is well within the experimental techniques of those skilled in the art of preparing test devices to determine the proper balance between size of the test pad, the strength of indicator reagent composition solutions, the amount of test sample, and the method of introducing the test sample to the test strip, such as by pipetting rather than dipping, in order to design a quantitative assay for total available chlorine utilizing the method and composition of the present invention.

The dried, twice-impregnated polyurethane film or filter paper then is secured to an opaque or transparent hydrophobic plastic handle with doublesided adhesive tape. The resulting test strip then is contacted with a test sample for a sufficient time to saturate the test pad with the sample. After waiting a predetermined time, such as from about 1 second to about 120 seconds, the test strip is examined, either visually or by instrument, for a response. The color transition, if any, of the test pad reveals the concentration of total available chlorine in the test sample.

In many cases, simple visual observation of the test strip provides the desired information. If more accurate information is required, a color chart bearing color spots corresponding to various known concentrations of total available chlorine can be prepared for the particular indicator reagent composition used in the test strip. The resulting color of the test strip after contact with the test sample then can be compared with the color spots on the chart to determine the concentration of total available chlorine in the test sample. If a still more accurate determination is required, a spectrophotometer or colorimeter can be used to more precisely determine the degree of the color transition. In addition, the dry phase test strip assay can be made quantitative by employing spectrophotometric or colorimetric techniques, as opposed to visual techniques, in order to more reliably and more accurately measure the degree of color transition, and, therefore, more accurately measure the concentration of total available chlorine in the test sample.

In accordance with one embodiment of the present invention, the following dry phase test strips were prepared to perform a dry phase assay for total available chlorine. A strip, a pad, or a sheet of a carrier matrix, like filter paper, first was immersed into an acetone solution including:

| First Immersion Solution | |
|---|---|
| Ingredient | Amount |
| Acetone | 40 g |
| TMB[1] | 0.5 g |
| 10% KLUCEL[2] | 5 g |
| Surfactant[3] | 0.02 g |

[1]tetramethylbenzidine indicator;
[2]a 10% aqueous solution of hydroxypropylcellulose, KLUCEL is available from Aqualon Co., Wilmington, DE; and
[3]AEROSOL OT, dioctyl sodium sulfosuccinate, available from Cytec Industries, West Paterson, NJ.

Excess solution was removed from the surface of the filter paper with a scraper bar.

The once-saturated or impregnated filter paper then was dried in a forced air oven having a temperature of about 45° C. to about 80° C. for about 5 minutes. After drying, the once-saturated or impregnated filter paper then was immersed into an aqueous solution including:

| Second Immersion Solution | |
|---|---|
| Ingredient | Amount |
| Water | 30 g |
| Citrate Buffer (1M) (pH 5.1) | 3 g |
| Peroxidase | 30 mg |
| 2.5% NATROSOL[4] | 1.5 g |

| Second Immersion Solution | |
|---|---|
| Ingredient | Amount |
| 2% BENECEL[5] | 3 g |

[4]a 2.5% aqueous solution of hydroxyethylcellulose, NATROSOL is available from Aqualon Co.; and
[5]a 2% aqueous solution of hydroxyethylmethylcellulose, BENECEL is available from Aqualon Co.

The twice-saturated or impregnated filter paper then was dried in an oven having a temperature of about 40° C. to about 80° C. for about 5 minutes. The dried and twice-saturated or impregnated filter paper then was backed with a double-sided adhesive, and slit into 0.2 inch (0.5 cm) wide ribbons. A ribbon of filter paper incorporating an indicator reagent composition of the present invention then is attached to a polystyrene plastic support by means of the double-sided adhesive. The plastic support, including the saturated or impregnated filter paper, then is slit into 0.2 inch (0.5 cm) wide strips. Accordingly, the plastic support includes a pad having dimensions of about 0.2 inch (0.5 cm) by about 0.2 inch (0.5 cm) of saturated or impregnated filter paper to provide a test pad comprising a filter paper carrier matrix incorporating an indicator reagent composition of the present invention.

In addition, it should be understood that an indicator reagent composition of the present invention demonstrates sufficient stability such that the carrier matrix can be saturated or impregnated by immersing the carrier matrix into a single aqueous solution, or a single aqueous acetone solution, including all of the essential and optional ingredients of the indicator reagent composition. However, the two-step method utilizing two immersions is preferred because certain indicator reagent composition ingredients have relatively low water solubilities, and a more stable color transition is observed.

To demonstrate the new and unexpected results achieved by the method of the present invention, dry phase test strips incorporating an indicator reagent composition of the present invention (Formulation #1) were used to assay standardized solutions containing available chlorine. Individual test strips were dipped into a series of standardized solutions, containing from 0.5 ppm to 5000 ppm available chlorine. The standardized solutions were prepared by diluting a 5.25% (by weight) sodium hypochlorite solution with water.

The standardized solutions were assayed for total available chlorine by contacting the test strip with a standardized solution for about one (1) second. The color of the test strips then was observed. Timing of the strip reaction is not critical. However, for consistency, the strip color was evaluated after 60 seconds in each test. It should be noted that the present test strips can detect 0.1 ppm or less total available chlorine by contacting the test strip with the test sample for 60 seconds, or can detect 0.05 ppm or less total available chlorine by contacting the test strip with the test sample for 120 seconds. Any trace of a blue color is considered a positive test for available chlorine. The test results are set forth in Table 1.

TABLE 1

| Dilution of 5.25% Sodium Hypochlorite Solution[6] | 1/10 | 1/20 | 1/50 | 1/100 | 1/200 | 1/500 | 1/1000 | 1/5000 | 1/10,000 | 1/50,000 | 1/100,000 |
|---|---|---|---|---|---|---|---|---|---|---|---|
| ppm of Available Chlorine | 5000 | 2500 | 1000 | 500 | 250 | 100 | 50 | 10 | 5 | 1 | 0.5 |
| Color Transition[7] | Brown | Black | Dark Blue | Deep Blue | Navy Blue | Sky Blue | Sky Blue | Aqua Blue | Light Blue | Lighter Blue | Positive Blue |

[6]diluting 1 volume part of aqueous 5.25% (by weight) sodium hypochlorite solution with indicated volume parts of water; and
[7]test strip was colorless prior to immersion into the standardized solution.

The results set forth in Table 1 show that a test strip of the present invention is capable of assaying for total available chlorine over the entire range of 0 to greater than 5000 ppm by providing a differentiable color response over this entire range. Accordingly, a single test strip can be used to ensure that a sanitizing solution has sufficient strength to perform its intended function, and that the residual chlorine (or residual peroxide) in rinse water is below toxic levels.

In particular, Table 1 shows that if the test strip shows any degree of blue color, then the rinse water contains a potentially toxic amount of free available chlorine, and, therefore, rinsing of the hemodialysis unit with deionized water should be continued. Similarly, if that same test strip is dark blue to black to brown, then the solution being pumped through the hemodialysis unit contains a sufficient amount of free available chlorine to sanitize the unit. The intermediate values for total available chlorine are important in other applications, for example, in restaurant sanitizing solutions or in swimming pools applications, to ensure that proper levels of total available chlorine are present.

The results in Table 1 also show that in the low concentration range (e.g., about 500 ppm or less) color differentiation between different total available chlorine concentrations is relatively easy to distinguish. The color transitions in the high range are particularly useful in ensuring that hemodialysis units are properly cleaned between patients because the sanitizing solution needed to clean the hemodialysis unit requires a free available chlorine concentration of at least 1000 ppm.

In other tests, the affect of a surfactant on the ability of an indicator reagent composition of the present invention to assay over a broad total available chlorine range also was investigated. As previously stated, it is desirable to extend an assay for total available chlorine to include a high detection range of 1000 ppm or greater. This was difficult to achieve using prior test strips unless the test sample was diluted to reduce the chlorine concentration to within the detectable range of the test strip. Test sample dilution is undesirable because of the time involved and because of the distinct possibility of dilution error, and, in turn, assay error.

An assay having a broad total available chlorine detection range allows the user to directly monitor, without dilution, the effective chlorine level of a sanitizing or disinfecting solution. In particular, a 1:10 dilution of a 5.25% sodium hypochlorite solution with water, which commonly is used in hemodialysis operations to sanitize the dialysis system, can be assayed using a present test strip. The problem with currently available test strips is that the detection ranges are narrow and confined to a specific range, typically 0 to 10 ppm, although some starch-iodine papers have a detection range of 10 to 200 ppm. In all cases, the detection range is confined to low or middle concentration range, and no present test strip has a detection range to assay for both low and middle concentration levels of total available chlorine, let alone a high concentration level of total available chlorine.

For example, when tetramethylbenzidene (TMB) is used as the indicator, the oxidized, blue form of TMB results in test samples having a low free available chlorine concentration. This blue form of oxidized TMB quickly converts into a higher oxidation state, and becomes yellow/brown in color. It has been found that surfactants, and especially anionic surfactants, prevent such a conversion, and, accordingly, the brown color form of oxidized TMB is formed only at much higher free available chlorine concentrations.

To demonstrate the effect of a surfactant, solutions containing different surfactants were individually impregnated onto filter paper, such as Schleicher & Schuell 903. The solutions contained the following ingredients, wherein the identity of the surfactant was varied:

| | |
|---|---|
| Acetone | 5 g |
| Tetramethylbenzidene | 0.5 g |
| Surfactant | 0.005 g. |

Filter paper was dipped in a solution, then dried at 65° C. for 5 minutes. The dried filter papers were made into strips by cutting into 0.2 inch squares, which were adhered to a plastic handle using double-side adhesive tape. The resulting test strips were dipped into solutions having different free available chlorine concentrations. The color of each test strip was visually observed and recorded. Table 2 summarizes the test results using different surfactants.

TABLE 2

Effect of Surfactant on Assay Range Using Tetramethylbenzidine

| Dilution Factor[6] | 1:10 | 1:50 | 1:500 | 1:5000 | 1:10,000 |
|---|---|---|---|---|---|
| Nonionic Surfactants[8] | | | | | |
| BRIJ 35 | Y[12] | Y | Y/Gr | Bl | Lt/Blue |
| TWEEN 20 | Y | Y | Y/Gr | Bl | Lt/Blue |
| TRITON X-100 | Y | Y | Y/Gr | Bl | Lt/Blue |
| Anionic Surfactants[9] | | | | | |
| DBS | Br | Bk/Bl | Bl | Bl | Lt/Blue |
| SDS | Br | Bk/Bl | Bl | Bl | Lt/Blue |
| DOSS | Br | Gr/Bl | Bl | Bl | Lt/Blue |
| Cholate | Br | Br | Bl | Bl | Lt/Blue |
| Benzoic acid[10] | Br | Bk/Bl | Bl | Bl | Lt/Blue |
| Lauric acid | Br | Bk/Bl | Bl | Bl | Lt/Blue |
| Caprylic acid | Br | Bk/Bl | Bl | Bl | Lt/Blue |
| Cationic Surfactants[11] | | | | | |
| CTAB | Y | Y | Gr | Gr | Gr |
| CPC | Y | Y | Y | Bl | Lt/Blue |
| Zwitterionic | | | | | |

TABLE 2-continued

Effect of Surfactant on Assay Range Using Tetramethylbenzidine

| Dilution Factor[6] | 1:10 | 1:50 | 1:500 | 1:5000 | 1:10,000 |
|---|---|---|---|---|---|
| Surfactants[11] | | | | | |
| Z-08 | Y | Y | Gr | Bl | Lt/Blue |
| CHAPS | Y | Y | Gr | Gr | Lt/Blue |
| Control | | | | | |
| None | Y | Y | Gr | Gr | Lt/Blue |

[8] BRIJ 35 — polyethylene glycol dodecyl ether (23 moles ethylene oxide), TWEEN 20 — polyethylene glycol sorbitan monolaurate (20 moles ethylene oxide), and TRITON X-100 — polyethylene glycol tert-octyl phenyl ether (9 moles ethylene oxide);
[9] DBS — dodecylbenzene sulfonate, SDS — sodium dodecylsulfate, DOSS — dioctyl sulfosuccininate, and cholate — sodium salt of cholic acid;
[10] benzoic acid is not a surfactant, but is capable of stabilizing color formation;
[11] CTAB — cetyltrimethylammonium chloride, CPC — cetylpyridinum chloride, Z-08 — Zwittergent 3-08, and CHAPS — 3,[(3-cholamidopropyl) dimethylammomio]-1-propane sulfonate; and
[12] color designations: Y — yellow; Br — brown; Bk — black; Dk — dark; Gr — green; Bl — blue; Y/Gr — yellowish green; Bk/Bl — black blue, Dk/Bl — dark blue, Lt/Bl — light blue.

As illustrated in Table 2, anionic surfactants have an excellent ability to prevent oxidized tetramethylbenzidine, that is blue in color, from being further oxidized and turning brown in color. The class of anionic surfactant present in an indicator reagent composition is not important, e.g., sulfate, sulfonate, carboxylate, phosphate, and similar hydrophilic moieties are useful. However, the hydrophobic moiety of the anionic surfactant can have an effect. The tests show that a linear hydrophobic moiety, alone or with phenyl groups, is slightly more effective in stabilizing the color of the indicator than a bulkier hydrophobic moiety, such as cholate or dioctyl sulfosuccinate. It is theorized that both the hydrophilic group, and the hydrophobic moiety of the surfactant interact with the indicator, thereby protecting the indicator from further oxidation, and further color change. Nonionic surfactants also were effective, in stabilizing the color transition, especially in the absence of polycarboxylic acid buffer, but cationic and zwitterionic surfactants failed to effectively prevent further oxidation of an oxidized indicator.

As previously stated, the indicator reagent composition is buffered in a pH range of about 5 to about 6. It also has been found that the identity of the buffer has an effect with respect to stabilizing the color transition and preventing the colored, oxidized form of the indicator from being further oxidized and turning the test strip brown. In particular, a citrate buffer and a phosphate buffer were equally effective with respect to stabilizing the color transition of a TMB indicator in the presence of free available chlorine, although the color of a test strip containing a citrate buffer has a brighter and cleaner blue color than a test strip containing a phosphate buffer. The following Table 3 illustrates the effect of different buffers on color stability of an indicator reagent composition using TMB as the indicator.

TABLE 3

Effect of Buffer on Color Stability

| Dilution Factor[6] | 1:10 | 1:50 | 1:500 | 1:5000 | 1:10,000 |
|---|---|---|---|---|---|
| Buffer (pH) | | | | | |
| Citrate (5.1) | Br[12] | Bk/Bl | Bl | Bl | Lt/Bl |
| Succinate (5.2) | Br | Bk/Bl | Bl | Bl | Lt/Bl |
| 2-Ketoglutarate (5.6) | Br | Br | Bl | Bl | Lt/Bl |
| Lactate (5.1) | Br | Dk/Bl | Bl | Bl | Lt/Bl |
| Phosphate (5.3) | Br | Bk/Bl | Bl | Bl | Lt/Bl |
| Borate (5.4) | Y | Y | Gr | Lt/Bl | Lt/Bl |

In addition, the ability of a peroxidase to stabilize the color transition of a test strip and catalyze the assay for total available chlorine was demonstrated by adding 50 milligrams of horseradish peroxidase to the second immersion solution of Formulation #1, preparing test strips, and using the test strips to assay for total available chlorine of solutions containing chloramine. The tests showed that peroxidase increased the reaction rate to convert bound chlorine to free chlorine, and the test strip underwent a complete color transition faster than a test strip lacking peroxidase.

From the visual assays and the data presented in Tables 1–3, it has been demonstrated that a particularly useful indicator is tetramethylbenzidine. An indicator reagent composition of the present invention that includes tetramethylbenzidine, in addition to a surfactant and a buffer to buffer the composition to a pH of about 5 to about 6, exhibits a sufficiently dramatic color transition, from light blue to brown, to provide a sensitive and accurate assay for total available chlorine in a test sample. The color transition also is sufficiently resolvable and differentiable, either visually or by instrument, such that an unknown concentration of total available chlorine in a test sample can be determined. Furthermore, it has been found that the indicator is stabilized by interaction with a surfactant, and that a catalyst can convert bound available chlorine to free available chlorine, such that the color transition endpoint is reached within about 1 second to about 2 minutes.

In accordance with an important feature of the present invention, the continuing and substantial problems in dry phase test strips for assaying a wide concentration range of total available chlorine, including the instability of the indicator, are essentially eliminated by the present invention. An indicator reagent composition of the present invention provides a differentiable response to total available chlorine over the concentration range of 0 to greater than 5000 ppm of the test sample. Therefore, accurate and reliable assays for total available chlorine in test samples can be performed by utilizing an indicator reagent composition and device of the present invention.

Obviously, many modifications and variations of the invention as hereinbefore set forth can be made without departing from the spirit and scope thereof, and, therefore, only such limitations should be imposed as are indicated by the appended claims.

What is claimed is:

1. A composition capable of exhibiting a detectable and measurable color transition in response to a total available chlorine concentration of 0 to greater than 5000 ppm, said composition comprising:

(a) an indicator capable of interacting with free available chlorine;

(b) a buffer;

(c) a nonionic surfactant, an anionic surfactant, or a mixture thereof; and (d) a carrier comprising water, wherein the composition has a pH of about 5 to about 6.

2. The composition of claim 1 wherein the indicator is present in a concentration of about 1 to about 200 millimoles per liter of the composition.

3. The composition of claim 1 wherein the indicator comprises a redox indicator, a heterocyclic azine indicator, or a mixture thereof.

4. The composition of claim 1 wherein the indicator is a benzidine-type indicator having a structure

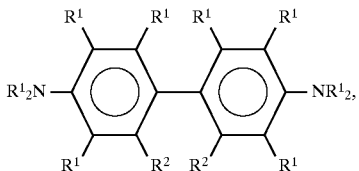

wherein $R^1$ and $R^2$ substituents, either the same or different, are selected from the group consisting of hydrogen, a lower alkyl group, a lower alkyloxy group, aryl, and aryloxy, or the $R^2$ substituents can be taken together to form $-(CH_2)_n-$, wherein n is 1 or 2.

5. The composition of claim 4 wherein the indicator is selected from the group consisting of benzidine, o-tolidine, o-dianisidine, 2,7-diaminofluorene, 3,3',5,5'-tetramethylbenzidine, 3,3',5,5'-tetra(alkyl)benzidine wherein the alkyl group contains two to about six carbon atoms, a nitrogen substituted benzidine, bis(N-ethylquinol-2-one)azine, and (N-methylbenzthiozal-2-one)(1-ethyl-3-phenyl-5-methyltriazol-2one)azine.

6. The composition of claim 1 wherein the buffer is present in a concentration of about 20 to about 600 millimoles per liter of the composition.

7. The composition of claim 1 wherein the buffer is selected from the group consisting of a polycarboxylic acid wherein the carboxyl groups are separated by two to five carbon atoms, citric acid, succinic acid, ketoglutaric acid, lactic acid, phosphate, borate, acetate, and mixtures thereof.

8. The composition of claim 1 wherein the surfactant is present in an amount of about 0.05% to about 1.5% by weight of the composition.

9. The composition of claim 1 wherein the nonionic surfactant has an HLB value of about 6 to about 25.

10. The composition of claim 1 wherein the nonionic surfactant is selected from the group consisting of an ethoxylated polysorbate, an ethoxylated alcohol, an ethoxylated phenol, a polyethylene glycol, a polypropylene glycol, an ethylene glycol-propylene glycol copolymer, a polybutylene glycol, and mixtures thereof.

11. The composition of claim 1 wherein the anionic surfactant comprises a sulfate, a sulfonate, a carbonate, a phosphate, or a carboxylate.

12. The composition of claim 1 wherein the anionic surfactant is selected from the group consisting of an alkyl sulfate, an alkyl ether sulfate, an alkyl ether sulfonate, a sulfate ester of an alkylphenoxy polyoxyethylene ethanol, an alpha-olefin sulfonate, a beta-alkyloxy alkane sulfonate, an alkyl arylsulfonate, an alkyl carbonate, an alkyl ether carboxylate, a fatty acid, a sulfosuccinate, an alkyl ether sulfosuccinate, a sarcosinate, an octoxynol phosphate, a nonoxynol phosphate, a taurate, a fatty tauride, a sulfated monoglyceride, a fatty acid amido polyoxyethylene sulfate, and mixtures thereof.

13. The composition of claim 1 wherein the anionic surfactant comprises an ammonium, monoethanolamine, diethanolamine, triethanolamine, isopropylamine, sodium, potassium, lithium, or magnesium salt of lauryl sulfate, dodecylbenzenesulfonate, lauryl sulfosuccinate, a lauryl ether sulfate, a lauryl ether carboxylate, lauryl sarcosinate, cocomethyl tauride, and a sulfosuccinate half ester amide, and mixtures thereof.

14. The composition of claim 1 wherein the carrier comprises 0% to about 90% by weight of the carrier of an organic solvent.

15. A method of determining total available chlorine content of an aqueous test sample containing 0 to greater than 5000 ppm total available chlorine, said method comprising:
  (a) contacting the aqueous test sample with an indicator reagent composition comprising:
    (i) an indicator capable of interacting with free available chlorine,
    (ii) a buffer,
    (iii) a nonionic surfactant, an anionic surfactant, or a mixture thereof, and
    (iv) a carrier comprising water, wherein the composition has a pH of about 5 to about 6; and
  (b) determining the total available chloride content of the aqueous test sample from the intensity and degree of a color transition of the indicator reagent composition, wherein the intensity and degree of the color transition are determined visually or instrumentally.

16. The method of claim 15 wherein the indicator reagent composition further comprises:
  (v) a catalyst selected from the group consisting of a peroxidase enzyme, iodide ion, and mixtures thereof; and
  (vi) a polymer.

17. The method of claim 15 wherein the aqueous test sample has a total available chlorine content of 0 to greater than 1000 ppm.

18. A method of determining the total available chlorine content of an aqueous sample containing 0 to greater than 5000 total available chlorine, said method comprising:
  (a) contacting the aqueous sample with an analyte detection device comprising a test pad, said test pad having incorporated therein an indicator reagent composition comprising:
    (i) an indicator capable of interacting with free available chlorine,
    (ii) a buffer,
    (iii) a nonionic surfactant, an anionic surfactant, or a mixture thereof, and
    (iv) a carrier comprising water, wherein the composition has a pH of about 5 to about 6; and
  (b) determining the total available chlorine content of the aqueous sample from the intensity and degree of a color transition of the indicator reagent composition.

19. A method of determining the total available chlorine content of an aqueous sample comprising:
  (a) contacting the aqueous sample with an analyte detection device comprising a test pad having incorporated therein:
    (i) an indicator capable of interacting with free available chlorine,
    (ii) a buffer to maintain a pH of about 5 to about 6,
    (iii) a nonionic surfactant, an anionic surfactant, or a mixture thereof, and
    (iv) a carrier comprising water; and
  (b) examining the analyte detection device for a color transition; and
  (c) correlating the color transition to the total available chlorine content of the aqueous sample.

20. The method of claim 19 wherein the aqueous sample has a total available chlorine content of 0 to about 5000 .

21. An analyte-detection device to determine the total available chlorine content of an aqueous test sample comprising:
   a support strip;
   a test pad; and
   an indicator reagent composition incorporated into the test pad, said reagent composition comprising:
      (a) an indicator capable of interacting with free available chlorine,
      (b) a buffer,
      (c) a nonionic surfactant, an anionic surfactant, or a mixture thereof, and
      (d) a carrier comprising water,
   wherein the composition has a pH of about 5 to about 5.5.

22. A composition capable of exhibiting a detectable and measurable color transition in response to a total available chlorine concentration of 0 to greater than 5000 ppm, said composition comprising:
   (a) an indicator capable of interacting with free available chlorine;
   (b) a buffer;
   (c) a nonionic surfactant, an anionic surfactant, or a mixture thereof;
   (d) a carrier comprising water;
   (e) a catalyst selected from the group consisting of a peroxidase enzyme, iodide ion, and mixtures thereof; and
   (f) a polymer,
   wherein the composition has a pH of about 5 to about 6.

23. A composition capable of exhibiting a detectable and measurable color transition in response to a total available chlorine concentration of 0 to greater than 5000 ppm, said composition comprising:
   (a) an indicator capable of interacting with free available chlorine;
   (b) a buffer;
   (c) a nonionic surfactant, an anionic surfactant, or a mixture thereof; and
   (d) a carrier comprising water,
   wherein the composition has a pH of about 5 to about 5.5.

24. A composition capable of exhibiting a detectable and measurable color transition in response to a total available chlorine concentration of 0 to greater than 5000 ppm, said composition comprising:
   (a) about 10 to about 150 millimoles per liter of the composition of a benzidine-type indicator;
   (b) about 50 to about 2000 millimoles per liter of the composition of a buffer selected from the group consisting of a polycarboxylic acid having carboxyl groups separated by two to five carbon atoms;
   (c) about 0.1 to about 1% by weight of the composition of an anionic surfactant; and
   (d) a carrier comprising water,
   wherein the composition has a pH of about 5.1 to about 5.5.

25. A method of determining the total available chlorine content of an aqueous sample containing 0 to greater than 5000 ppm total available chlorine, said method comprising:
   (a) contacting the aqueous sample with an analyte detection device comprising a test pad, said test pad having incorporated therein a composition of claim 34; and
   (b) determining the total available chlorine content of the aqueous sample from the intensity and degree of a color transition of the composition.

26. The composition of claim 22 wherein the catalyst is present in an amount of 0 to about 1000 ppm.

27. The composition of claim 22 wherein the peroxidase enzyme is horseradish peroxidase.

28. The composition of claim 22 wherein the iodide ion is present as an alkali metal iodide.

29. The composition of claim 28 wherein the iodide ion is present in an amount of 0 to about 20 ppm.

30. The composition of claim 22 wherein the polymer is present in an amount of 0% to about 4% by weight of the composition.

31. The composition of claim 22 wherein the polymer is selected from the group consisting of polyvinylpyrrolidone, an ester of a PVM/MA copolymer, polyvinyl alcohol, gum arabic, gelatin, algin, carrageenan, casein, albumin, methyl cellulose, hydroxypropylcellulose, hydroxyethylcellulose, hydroxybutylcellulose, sodium carboxymethylcellulose, and mixtures thereof.

32. The composition of claim 24 further comprising:
   (e) 0 to about 10 ppm iodide ion, 0 to about 1000 ppm peroxidase enzyme, or a mixture thereof; and
   (f) 0% to about 3% by weight of the composition of a cellulose-type polymer.

* * * * *

UNITED STATES PATENT AND TRADEMARK OFFICE
CERTIFICATE OF CORRECTION

PATENT NO. : 5,811,254

DATED : September 22, 1998

INVENTOR(S) : Wen H. Wu

It is certified that error appears in the above-identified patent and that said Letters Patent is hereby corrected as shown below:

Column 2, line 36, "5.25" should be --5.25%--

Column 11, line 21, "Iodine" should be --Iodide--

Column 11, lines 52 & 53, "polyvinylpyrrolidone pyrrolidone of" should be --polyvinylpyrrolidone of--

Column 19, line 21, "dimethylammomio" should be --dimethylammonio--

Column 21, line 29, " -2one " should be -- -2-one --

Column 22, line 19, "chloride" should be --chlorine--

Column 22, line 36, "5000" should be --5000 ppm--

Column 22, line 67, "5000" should be --5000 ppm--

Signed and Sealed this

Thirtieth Day of November, 1999

Q. TODD DICKINSON

Attest:

Attesting Officer

Acting Commissioner of Patents and Trademarks